United States Patent
Ilan et al.

(10) Patent No.: US 11,484,623 B2
(45) Date of Patent: Nov. 1, 2022

(54) DRY PAD COMPRISING THROMBIN AND PECTIN

(71) Applicant: Omrix Biopharmaceuticals Ltd., Rehovot (IL)

(72) Inventors: Erez Ilan, Kibbutz Netzer Sereni (IL); Yotam Gurman, Kibbutz Or Haner (IL); Ronen Eavri, Binyamina (IL); Elya Dekel, Tel Aviv (IL)

(73) Assignee: Omrix Biopharmaceuticals Ltd., Rehovot (IL)

( * ) Notice: Subject to any disclaimer, the term of this patent is extended or adjusted under 35 U.S.C. 154(b) by 138 days.

(21) Appl. No.: 14/519,699

(22) Filed: Oct. 21, 2014

(65) Prior Publication Data

US 2015/0147312 A1 May 28, 2015

Related U.S. Application Data

(60) Provisional application No. 61/908,877, filed on Nov. 26, 2013.

(30) Foreign Application Priority Data

Nov. 26, 2013 (IL) .......................................... 229645

(51) Int. Cl.
*A61L 15/44* (2006.01)
*A61L 15/28* (2006.01)
*A61L 15/38* (2006.01)

(52) U.S. Cl.
CPC ............... *A61L 15/44* (2013.01); *A61L 15/28* (2013.01); *A61L 15/38* (2013.01); *A61L 2300/418* (2013.01)

(58) Field of Classification Search
None
See application file for complete search history.

(56) References Cited

U.S. PATENT DOCUMENTS

| | | | |
|---|---|---|---|
| 4,265,233 A | 5/1981 | Sugitachi et al. | |
| 4,292,972 A | 10/1981 | Pawelchak et al. | |
| 4,813,942 A * | 3/1989 | Alvarez | A61L 15/42 424/445 |
| 5,688,923 A | 11/1997 | Gerrish et al. | |
| 6,290,565 B1 | 9/2001 | Galyean, Iii et al. | |
| 6,649,162 B1 * | 11/2003 | Biering | A61L 15/225 128/DIG. 22 |
| 7,019,191 B2 | 3/2006 | Looney et al. | |
| 8,226,970 B2 * | 7/2012 | Ahlers | A23J 3/06 264/176.1 |
| 2004/0224767 A1 | 11/2004 | Forsse | |
| 2006/0159733 A1 * | 7/2006 | Pendharkar | A61K 31/715 424/445 |
| 2006/0172000 A1 * | 8/2006 | Cullen | A61L 15/225 424/445 |
| 2008/0260810 A1 | 10/2008 | Zhang et al. | |
| 2012/0282320 A1 | 11/2012 | Scherr | |

FOREIGN PATENT DOCUMENTS

| | | |
|---|---|---|
| CN | 1867364 A | 11/2006 |
| GB | 708148 | 4/1954 |
| JP | 2003-531682 A | 10/2003 |
| WO | WO 97/30093 | 8/1997 |
| WO | 01/82937 A1 | 11/2001 |

OTHER PUBLICATIONS

Mishra et al. Pectin Based Formulations for Biomedical Applications: A Review (2012), Asian J of Pharmaceutical and Clincial Research, vol. 5, No. 4: 1-7 (Year: 2012).*
Cole DJ et al. "A pilot study evaluating the efficacy of a fully acetylated poly-N-acetyl glucosamine membrane formulation as a topical hemostatic agent". Surgery. Sep. 1999;126(3):510-7.
Prade RA et al. 'Pectins, pectinases and plant-microbe interactions' Biotechnol Genet Eng Rev. 1999 vol. 16 pp. 361-391.
International Preliminary Report on Patentability re: PCT/IL2014/000055 dated May 31, 2016.
International Search Report re: PCT/IL2014/000055 dated Feb. 5, 2015.

* cited by examiner

*Primary Examiner* — Teresa E Knight
(74) *Attorney, Agent, or Firm* — David R. Crichton

(57) ABSTRACT

The present invention is directed to a dry pad comprising pectin, a divalent cation and thrombin and to its preparation. Preferably, the density of pectin in the dry pad of the invention ranges from about equal to or higher than 1% to lower than 7% (w/v). The pad according to the invention comprises pectin having a low methoxyl content.

3 Claims, No Drawings

DRY PAD COMPRISING THROMBIN AND PECTIN

FIELD OF THE INVENTION

The invention relates to a thrombin-pectin pad and preparation thereof.

BACKGROUND OF THE INVENTION

Pectin is a natural polysaccharide extracted from plant substance. Pectin consists mainly of a linear chain of linked monomers of D-galacturonic acid (GalA) joined in chains by Alpha-(1-4) glycosidic linkage. These GalA monomers have an esterified carboxyl group ($COOCH_3$) side chain that can be substituted by three different side chains: Carboxyl group (COOH), Hydroxyl groups (OH), and Amino groups ($NH_3$) yielding pectins with different characteristics [Prade R A et al. Pectins, pectinases and plant-microbe interactions Biotechnol Genet Eng Rev. 1999]. The type of side chain is determined by a chemical reaction, facilitated by specific enzymes (based on the side chain); and by the solution conditions (e.g. pH level, presence of different saccharides, ion composition etc.).

There are two main pectin types: high methoxyl (HM) pectin and low methoxyl (LM) pectin. The distinction between these two groups is based on the ratio between the esterified GalA monomers and the total GalA monomers (referred to as "Degree of Esterification"-DE). Typically, DE's values for commercial HM pectins range from 60 to 75% and for LM pectins from 20 to 40%.

Pectin is used in the food industry e.g. as a thickening agent and in the medical industry e.g. as a pill coating material.

Gel formation properties of the two pectin types:

Addition of water to HM pectin powder under the following conditions results in gel formation: a pH of about 3, heat (a temperature of 75-80° C.) and the presence of soluble solids e.g. polysaccharides at a concentration of equal to or greater than 65%. The addition of polysaccharides reduces the pectin-water interaction and creates a pectin-saccharide interaction instead thereby contributing to the gelling activity. In contrast to HM pectins, LM pectins form a gel at a wider pH range (2.5-6.5), and the gel formation is independent of the polysaccharides content and temperature level. LM pectins require the presence of divalent cations (e.g. calcium; about 30-40 mg calcium per 1 gr pectin) for proper gel formation. The mechanism for LM pectin gelation involves formation of intramolecular bonds between the Hydroxyl and Carboxyl side chain groups. This structure is referred to as an "egg box" model, in which the calcium is trapped within the structure and a firmer gel is formed.

HM pectin type has a low content of Carboxyl side chain groups and lack of negatively charged Carboxyl side chain groups due the acidic pH required for gel formation (hydrogen is not released at acidic pH), therefore the addition of the positively charged calcium ion does not result in gel formation nor in the sterical formation of the "egg box" structure.

Several publications relate to compositions comprising pectin with or without thrombin:

US 2012/0282320 relates to the composition of a hemostatic powder that can be utilized as a wound dressing to stem bleeding. The hemostatic powder comprises a silver pectate moiety. According to the description the pectin utilized should be amendable to react with soluble calcium salt and produce an insoluble calcium pectate. Exemplified is a composition of a hemostatic powder that comprises 2.3% silver pectate. The publication explicitly indicates that use of a hemostatic powder as opposed to a lyophilized dressing is superior.

U.S. Pat. No. 7,019,191 discloses a lyophilized hemostatic wound dressings containing a fabric substrate and a porous, water-soluble or water-swellable polymeric matrix disposed on and through the substrate and to methods of making such hemostatic wound dressings. Polysaccharides is listed as one possible option of water-soluble or water-swellable polymer (amongst 17 possibilities); and pectin is listed as a possible polysaccharide amongst 35 possible polysaccharides. It is mentioned that the dressing can carry e.g. thrombin, fibrinogen and fibrin.

GB 708148 relates to hemostatic preparations and process for their manufacture. The inventors found that addition of basic acridine derivatives to thrombin preparations increases the activity of thrombin. The patent discloses pectin and pectin derivatives as a possible option to include in a thrombin preparation. Exemplified is a hemostatic preparation of a freeze-dried pectin-thrombin solution. The hemostatic preparation comprises 10% pectin.

U.S. Pat. No. 4,265,233 discloses a wound healing material having blood coagulation Factor XIII fixed thereto. This material promotes the formation of stabilized fibrin at a wound site. According to the description, preferably thrombin is fixed to the material together with Factor XIII. The material is in the form of a monofilament, a fibrous assembly, a film or a sponge. Pectin is mentioned as one option (out of an enormous list) which can make up the structure. The patent relates to bonding of Factor XIII and thrombin to various structures e.g. pectin structure.

U.S. Pat. No. 4,292,972 relates to a lyophilized foam sponge product having medically useful hemostatic and adhesive properties formed from the hydrocolloids, gelatin, pectin, and sodium carboxymethylcellulose and having a density of from about 0.01 to about 0.10 grams/cc. The gelatin is present at from about 20% to about 80% by weight of the final product and the pectin and sodium carboxymethylcellulose are each present at from about 10% to about 50% by weight of the final product. The product is prepared by forming an aqueous colloidal dispersion of hydrocolloids, aerating or foaming, freezing, and lyophilizing.

US 2008/0260810 relates to a hemostat comprising an absorbable foam, an absorbable woven or knitted fabric, thrombin and fibrinogen. According to the description, the absorbable foam may be a biocompatible, water-soluble, or water-swellable polymer. Preferred biocompatible, water-soluble, or water-swellable polymers used to fabricate the foam include polysaccharides. Pectin is mentioned as a possible polysaccharide amongst a vast list of possibilities. The application exemplifies a foam comprising carboxymethyl cellulose (as a water-soluble, or water-swellable polymer) and albumin (as a foaming agent/surfactant) attached to an oxidized regenerated cellulose fabric, and thrombin and fibrinogen incorporated into or sprayed onto the foam.

U.S. Pat. No. 5,688,923 relates to a polyvalent cation crosslinked pectin fiber composition composed of a calcium sensitive low methoxyl (LM) pectin useful in making wound dressings for topical applications.

Thrombin is a serine protease that catalyzes the conversion of soluble fibrinogen to insoluble fibrin. In surgery, oftentimes, liquid thrombin serves as a standalone product to stop bleeding by conversion of intrinsic fibrinogen to fibrin at an active bleeding site. However, liquid thrombin can be washed away from the bleeding site by oozing blood and thus the use of standalone thrombin may be less effective. To overcome this problem and physically retain thrombin on the active bleeding site, a pad, a sponge or a patch including the thrombin can be advantageously used.

Several publications describe the use of a dried foam sponge formed from an animal source protein (e.g. collagen or gelatin) in combination with thrombin for hemostatic use. However, production of sponges from animal source is a costly procedure whereas producing a sponge from a plant substance is cost saving.

Moreover, animal derived substances may carry a risk of transmitting infectious agents such as viruses.

The present invention is directed to a pad overcoming these and other deficiencies in the pads of the art.

SUMMARY OF THE INVENTION

The invention relates to a dry pad comprising pectin, a divalent cation e.g. calcium and thrombin and to its preparation. Preferably, the density of pectin in the dry pad of the invention ranges from about 1% to lower than 7% (w/v). The pad according to the invention comprises pectin having a low methoxyl content (named herein as "LM pectin").

Advantageously, the pad prepared according to the invention is homogeneous, has high liquid/blood absorbance ability, is malleable since it can be easily manipulated to conform to the shape of a body organ without breaking, exhibits increased adhesion to the target tissue, and can stay intact during manipulation and handling. Due to the malleability or adaptability of the pad it can be applied in a wide variety of organs having different structures and shapes.

Of note, the pad prepared according to the invention has improved adhesive properties. It can be used for promoting the formation of fibrin at a bleeding site and thereby enhance hemostasis (e.g. by the action of thrombin present within the pad on fibrinogen originated from the patient's blood).

In one embodiment of the invention, the pectin density within the dry pad is higher than 1% to lower than 7% (w/v).

In another embodiment of the invention, the pectin density within the dry pad is from about 1% to about 5% (w/v).

In a further embodiment, the pectin density within the dry pad is from about 1% to lower than 5% (w/v).

Yet in another embodiment of the invention, the pectin density within the dry pad is from about 3% to lower than 5% (w/v).

Yet in another further embodiment of the invention, the pectin density within the dry pad is about 3% (w/v).

In one embodiment of the invention, the pad is prepared by the following steps:
a—providing LM-pectin, a divalent cation, and thrombin;
b—mixing the pectin, divalent cation, and thrombin to bring pectin to a concentration of about 1% to lower than 7% (w/v) under conditions that allow homogenous gel formation; and
c—drying the gel.

In one embodiment of the invention, step b is carried out by first mixing thrombin with the divalent cation followed by addition of pectin.

In another embodiment of the invention, the divalent cation is calcium.

The invention also relates to a method of attenuating wound bleeding in a patient comprising applying the pad according to the invention to the wound, thereby attenuating the wound bleeding.

DESCRIPTION OF EMBODIMENTS OF THE INVENTION

In one aspect, the present invention provides an improved dry pad comprising pectin, a divalent cation and thrombin.

It was found according to the invention that a dry pad comprising a specific type of pectin at a specific concentration and in combination with thrombin enables formation of an improved dry pad that enables to absorb and hold within its interstices blood and other fluids and stop bleeding by formation of fibrin at the site of injury.

The pad according to the invention comprises low methoxyl (LM) pectin at densities ranging from about 1 to lower than 7% (w/v), from higher than 1% to lower than 7% (w/v), from about 1% to about 5% (w/v), from about 1% to lower than 5% (w/v), from higher than 1% to lower than 5% (w/v), from about 3% to lower than 5% (w/v) or about 3% (w/v).

The term pectin percent used throughout the application means pectin weight per volume (w/v).

For example, dry pads comprising pectin at densities ranging from about 1 to lower than 7% (w/v) means pectin at a density range from about 10 mg/cm$^3$ to lower than 70 mg/cm$^3$.

As used herein the term "about" refers to ±2%.

The term "improved dry pad" relates, for example, to a pad which enables to effectively stop bleeding e.g. mild, moderate, severe or brisk bleeding; has the ability to easily conform to the shape of a body surface without braking; exhibits increased adhesion to the target tissue; has high liquid/blood absorbance ability. The terms "stop bleeding" and "hemostasis" are interchangeable.

By "high liquid/blood absorbance ability" it is meant, for example, that the pad can absorb and hold within its interstices, many times its weight of blood and other fluids and/or can absorb blood and other fluids rapidly e.g. to absorb 30-folds its own weight within 30 seconds.

The term "hemostasis" refers to the ability of an agent to stop the bleeding from an injured blood vessel and/or to contribute to keeping the blood contained within the blood vessel.

It was found that a pad according to the invention has the ability to easily conform to the shape of the body surface while maintaining its structure and not break; is sticky and exhibits increased adhesion to the target tissue; has increased porosity which enables efficient absorption of liquid/blood into the pad; and stay intact during manipulation and handling.

Advantageously, the dry pad according to the invention is homogeneous, has high liquid/blood absorbance ability, can easily be manipulated and conformed to the shape of the body organ without breaking; exhibits increased adhesion to the target tissue; and can stay intact during manipulation and handling. The adaptability of the pad allows its application in a wide range of organs having different structures and shapes.

The term "homogenous", in this context of a pad, means that thrombin and pectin are substantially uniformly dispersed throughout the dry pad. Advantageously, different regions of the pad have approximately the same biological activity.

The term "dry" refers to a pad comprising a liquid content of equal to or less than 3% by weight based on the total weight of the dry composition (w/w). Advantageously, pectin is a plant derived polysaccharide and thus a pad formed with pectin may minimize the risk of viral and/or unknown pathogens transmission.

Also, the use of pectin, which is extracted from plants, in pharmaceutical products is of advantage since it is a non-immunogenic substance and is also a cost effective material with a long safety record.

In one embodiment of the invention, the divalent cation in the dry pad is calcium e.g. at a density range of 0.1-100 mg/cm$^3$ such as at a density of 4.5-7.5 mg/cm$^3$. In one embodiment of the invention, the calcium density within the pad is 4.5 mg/cm$^3$. In another embodiment of the invention, the calcium density within the pad is 7.5 mg/cm$^3$.

The thrombin density in the pad can be in the range of 10-1000 IU/cm$^3$ e.g. the density can be of about 340 IU/cm$^3$ or 680 IU/cm$^3$.

Typically, the pad of the invention can be stored at non freezing temperature storage conditions (e.g. at a temperature of 2-8° C. and up to room temperature or at a temperature of less than 37° C.) over a relatively long period of time while retaining its biological activity. "Room temperature" is meant to include temperature of about 20° C. to about 28° C., or 22° C. to about 26° C.

In one embodiment of the invention, the pad can be stored for 2 years at room temperature.

In another aspect, the invention relates to a method for preparing a dry pad according to the invention.

In one embodiment of the invention the method comprises the following steps:
  a—providing LM-pectin, a divalent cation, and thrombin;
  b—mixing the pectin, divalent cation, and thrombin to bring pectin to a concentration of about equal to or higher than 1% to lower than 7% (w/v) under conditions that allow homogenous gel formation; and
  c—drying the gel.

The concentration of pectin can range from about 1 to lower than 7% (w/v), from higher than 1% to lower than 7% (w/v), from about 1% to about 5% (w/v), from about 1% to lower than 5% (w/v), from higher than 1% to lower than 5% (w/v), from about 3% to lower than 5% (w/v) or about 3% (w/v).

In some embodiments, pads were prepared generally as described below. As a first step, different pectin stock solutions having a concentration of about 1.5 to 15% (w/v) (15-150 g/L) were prepared by dissolving LM pectin powder in Double Distilled Water (DDW) at 40-70° C. while stirring at 1300 RPM for 3-6 hours until the solution was homogenous as determined by a visual inspection. A solution having a pH of 3.5-5.5 was obtained. Next, 0.5M NaOH was added to form a pH of about 7.0. In the next step, the pectin stock solutions were stored at 4° C. overnight (14-18 hours) for stabilization of the pectin solution. In the next step, 1.7 ml thrombin (from EVICEL® Fibrin Sealant) and 25 µl 10.8M calcium chloride (CaCl$_2$) were mixed together and then the formed mixture was mixed with 3.3 ml of each pectin stock solution—1.5, 4.5, 7.5, 10.5 and 15%—to form pectin gels having a final pectin concentrations of about 1, 3, 5, 7 and 10% (w/v) (10-100 g/L), respectively. Mixing of the thrombin with CaCl$_2$ and then with pectin stock solution was carried out at room temperature (20-25° C.). Mixing of the thrombin-CaCl$_2$ solution with the pectin solution was carried out using two syringes (see elaboration below), the solutions were transferred between the two syringes 10-15 times. A final volume of 5 ml was obtained and the final mixture was poured into a lyophilization glass cup having the following dimensions: 25 mm height and 25 mm in diameter. The lyophilization glass cup was placed in the lyophilizer and lyophilized to form a dry pad having a water content of ≤3%. The different dry pads (after the lyophilization step) comprised a density of about: 1, 3, 5, 7 or 10% (w/v) (10-100 mg/cm$^3$) pectin, 340 IU/cm$^3$ thrombin and 7.5 mg/cm$^3$ calcium. The height of the dry pads was in the range of 10-14 mm and 25 mm in diameter.

In another embodiment a dry pad comprising a density of 3% (w/v) pectin (30 mg/cm$^3$) was prepared as follows:

2.25 gr LM pectin powder was dissolved in 48.5 ml DDW thereby obtaining a pectin stock solution at a concentration of 4.5% (w/v). The dissolution was carried out at 40° C.-70° C. with stirring at 1300 RPM for 3-6 hours (until the solution was homogenous as determined by a visual inspection). A solution having a pH of 3.5-5.5 was obtained. After dissolution, the pectin stock solution was titrated with 0.5M NaOH (about 2 ml) to a pH of about 7.0.

In the next step, the pectin stock solution was stored at 4° C. overnight (14-18 hours) for stabilization of the pectin solution.

In the next step, 1.7 ml thrombin, which includes 40 mM CaCl$_2$, were mixed with 25 µl 10.8M CaCl$_2$ (obtaining a final CaCl$_2$ concentration of 67.5 mM in the thrombin solution). The thrombin-calcium mixed solution (about 1.7 ml) was then mixed with 3.3 ml pectin stock solution (having a concentration of 4.5% w/v) to form a gel. Mixing of the thrombin with CaCl$_2$ and then with pectin stock solution was carried out at room temperature (20-25° C.).

Mixing was carried out by using two 5 ml syringes connected to one another via a 3-way-stopcock—one syringe with the thrombin-calcium solution, and the other with the pectin stock solution. The solutions were transferred between the two syringes 10-15 times. Following mixing, the mixed solutions (5 ml in volume) were poured into lyophilization cups (same dimensions as above), accessible bubbles formed on the upper surface of the gel were discarded using a needle, and the cups were then transferred into a lyophilizer and lyophilized.

The final density of pectin, thrombin and Calcium in the formed pad was 3% (w/v) (30 mg/cm$^3$), 340 IU/cm$^3$ and 7.5 mg/cm$^3$, respectively.

Following the lyophilization procedure, the pads were stored in a closed compartment with a desiccant at room temperature (20-25° C.).

In some embodiments, the solution volume of the pectin, thrombin and/or calcium are increased at about 1 to 20-folds to obtain bigger pads and/or more pads.

For liquid and gel substances, a pectin concentration of about 1% to lower than 7% (w/v) means pectin at a concentration range of about 10 g/L to lower than 70 g/L.

The term "mixing" refers to the blending of or stirring of the components (e.g. pectin, divalent cation, and thrombin) together.

The term "mixing under conditions that allow homogenous gel formation" refers to blending or stirring the components in specific condition(s) e.g. in a manner (e.g. a specific mixing sequence of the components) and/or in an environment (e.g. having a specific pH, having a specific temperature and/or avoiding bubble formation) that enables formation of a uniform gel. In one embodiment, such conditions comprise first mixing thrombin with the divalent cation and afterwards adding pectin.

The term "homogenous", in the context of a gel, means that thrombin and pectin are substantially uniformly dispersed throughout the gel substance (prior to drying the pad). For example, different regions of the gel have approximately the same thrombin and pectin concentration. A homogenous gel can be obtained e.g. by thoroughly and gently mixing the pectin solution with the thrombin solution containing divalent cations. In one embodiment, the mixing is carried out by using two syringes connected to each other, one comprising the pectin solution and the other comprising the thrombin solution. Homogenous gel can be obtained e.g. by eliminating the presence of a large number of bubbles and/or of large bubbles within the gel e.g. by using a needle; and/or by avoiding the presence of liquid above the formed gel resulting from improper mixing. Mixing can also be carried out by using agitators which thoroughly mix the solution.

The term "gel" refers to a semirigid jelly-like material in which molecules of a liquid are dispersed within a solid and in which the solid is the continuous phase and the liquid is the discontinuous phase. Typically, gels are substantially dilute cross-linked system, which do not flow. Gels are mostly liquid, but have solid's characteristics due to the presence of a three-dimensional cross-linked network within the liquid.

The LM-pectin, divalent cation, and thrombin can be provided as solutions. The total solids in the thrombin solution can be about 1-45 mg per ml.

In one embodiment of the invention, the divalent cation is provided within the thrombin solution. In another embodiment of the invention, the divalent cation is provided as a separate solution.

The drying step can be carried out by any procedure known in the art which does not degrade or denature the active ingredients e.g. thrombin which are sensitive to thermal procedures including, but not limited to, vacuum drying, lyophilization and air drying such as room temperature drying.

In one embodiment, drying can be carried out by lyophilization. The term "lyophilization" typically refers to the process of freezing a mixture and then reducing the concentration of water e.g. by sublimation to levels which do not support biological or chemical reactions.

Typically, following the lyophilization, a "solid cake" is obtained. The terms "cake", "solid cake", "dry composition" refer to a porous and spongy structure-like composition resulting from the lyophilization process.

It was shown that following the lyophilization process the formed cake supported its own structure i.e. the structure and volume of the gel substance and of the solid composition were substantially the same. This parameter can be evaluated by gently compressing the pad and evaluating the pad's fractions left on the glove. The pads should advantageously maintain their structure and stay intact during manipulation and handling. It is important to keep a balance between a pad that can easily conform to the shape of the body but can still maintain its structure and not break.

As used herein, the terms "dry composition" and "dry pad" are interchangeable and refer to a composition having a water content of equal to or less than about 3% (w/w).

The pectin used according to the invention can be derived (e.g. extracted or isolated) from any plant or portion thereof (e.g. seeds, leaves, stalks, flowers, roots, and/or stems). The pectin can have a variable level of purity and can also comprise other components extracted or isolated from the plant or the portion thereof in addition to pectin.

The pectin can have a degree of Esterification in the range of about 20% to 75%, and a degree of Amidation in the range of about 15% to 30%.

In one embodiment of the invention, the degree of Esterification is in the range of about 26 to 27%. In another embodiment of the invention, the degree of Amidation is in the range of about 20 to 22%.

The term "degree of Esterification" refers to the ratio between the esterified GalA monomers and the total GalA monomers.

The term "degree of Amidation" refers to the ratio between the amidated GalA monomers and the total GalA monomers.

In one embodiment of the invention, the pad comprises an additional haemostatic agent. The term "haemostatic agent", as used herein, refers to the ability of the agent to control, reduce or stop capillary, venous, or arteriole bleeding, including mild, moderate, severe or brisk bleeding, within an effective time, as recognized by those skilled in the art. Examples of haemostatic agents include but are not limited to, prothrombin, fibrin, fibronectin, Factor X/Xa, Factor VII/VIIa, Factor IX/IXa, Factor XI/XIa, Factor XII/XIIa, factor XIII, factor VIII, vitronectin, tissue factor, von Willebrand Factor, plasminogen activator inhibitor, platelet activating agents, synthetic peptides having hemostatic activity, derivatives of the above and any combination thereof.

The term "mild" refers to cases of bleeding where small volumes and a low rate of bleeding occur. In mild bleeding, the bleeding can stop on its own or with pressure, the bleeding can stop or slow to an ooze or trickle after about 10-20 minutes of pressure, and/or it may ooze or trickle for up to 40 minutes.

Examples for mild bleeding include, but not limited to, bleeding due to damage in a small area on a body organ such as the skin where anticoagulant medication is not prescribed and no damage is inflicted on large veins or arteries. Typically, in mild bleeding, hemostasis will be achieve spontaneously by the native blood clotting mechanism.

The term "moderate" refers to cases of bleeding where large volumes of blood are lost in either low rates of bleeding over a long period of time or when medium rates of bleeding are lost over a short time period. Typically, in moderate bleeding, the bleeding slows or stops with about 15 min. pressure but starts again when pressure is removed, and/or the blood may soak through a few bandages, but it is not fast or out of control.

Examples for moderate bleeding include, but not limited to, bleeding due to damage in a large area on a body organ such as the skin or in cases where small areas are damaged in organs receiving a rich supply of blood. Typically, in moderate bleeding, failure in achieving hemostasis will result in death in minutes to hours. The term "severe or brisk bleeding" refers to cases of bleeding where high volumes and a high rate of bleeding occur. Oftentimes, in severe bleeding blood pump from the wound, the bleeding does not stop or slow down with pressure, and/or blood is quickly soaking through bandage after bandage.

Examples of sever and brisk bleeding include, but are not limited to, bleeding due to arterial puncture, liver resection, kidney resection, hemophiliacs and patient receiving anti-coagulant medication and the like. Typically, in severe or brisk bleeding, failure in achieving hemostasis will result in death in seconds to minutes.

The effectiveness of the pad in stopping bleeding can be assessed by using an in-vivo animal model experiment. For example, a Rat kidney hemorrhage model (a model of severe bleeding) and a Swine spleen hemorrhage model (a model of mild to moderate bleeding) as described in the Examples below.

It was found according to the invention that a dry pad comprising thrombin and equal to or higher than 1% to lower than 5% (w/v) LM pectin effectively stopped severe bleeding, and that a dry pad comprising thrombin and equal to or higher than 1% to lower than 7% (w/v) LM pectin effectively stopped mild to moderate bleeding.

In one embodiment of the invention, the dry pad comprises thrombin and LM pectin at a density of about 1% to lower than 5% (w/v) and can be used for mild to severe bleeding.

In one embodiment of the invention, the dry pad is for use in mild to moderate bleeding and comprises thrombin and LM pectin at a density of about 1% to lower than 7% (w/v).

In one embodiment of the invention, the dry pad is for use in severe bleeding and comprises thrombin and LM pectin at a density of about 1% to lower than 5% (w/v).

It was also found according to the invention that the performance of a pectin pad in stopping bleeding may be enhanced by increasing the thrombin density e.g. the performance of a pad comprising 3% (w/v) pectin and 340 IU/cm$^3$ thrombin was enhanced when increasing the pectin density within the pad to 680 IU/cm$^3$ thrombin.

In one embodiment of the invention, the density of thrombin can be increased at least twice to increase the performance of the pectin pad.

The pad of the invention can be prepared and provided in a variety of sizes and shapes such as square, polygonal, spherically, conically, cubically, oval, rectangular, or cylindrically, depending on the intended use. For example, the pad of the invention can be prepared in rectangular shape with sizes of (width×length) 5×10 cm, 10×10 cm, both with a height of 1 cm. In another example, the pad of the invention can be prepared in a circular shape with diameters of 2 cm, 4 cm, or 6 cm, all having a height of 1 cm.

The pad according to the invention can be applied to the site of bleeding as is and stop bleeding by conversion of intrinsic fibrinogen to fibrin at the active bleeding site.

The pad can be applied onto the desired site and held under pressure for a period of time, e.g. at a period of time ranging from 30 seconds to 4 minutes, which is sufficient for clotting to occur at the interface between the pad and the application site and for bleeding to be substantially ceased.

The disclosure of ranges in the description of the invention is easily understood by the skilled person. It means the disclosure of continuous values and figures between the limits of the ranges, including the limiting figures and values. For example, if a range is given of from about 1% to lower than 7% (w/v), it is meant at least 1, 1.5, 2, 2.5, 3, 3.5, 4, 4.5, 5, 5.5, 6, 6.5, and/or lower than 7% (w/v), with all combinations of intermediate sub ranges such as 1 to 6.75% (w/v). For example, if a range is given of from higher than 1% to lower than 7% (w/v), it is meant at least 1.1, 1.2, 1.3, 1.4, 1.5, 1.6, 1.7, 1.8, 1.9, 2, 2.5, 3, 3.5, 4, 4.5, 5, 5.5, 6, 6.5, and/or lower than 7% (w/v), with all combinations of intermediate sub ranges such as 1 to 6.75% (w/v).

In another aspect, the invention relates to a method of attenuating wound bleeding in a patient comprising applying the pad according to the invention to the wound, thereby attenuating the wound bleeding.

By "attenuating wound bleeding" it is meant e.g. that the blood loss from an injured tissue and/or organ is reduced, diminished or eliminated.

The term "wound" includes, but is not limited to, arterial puncture, liver resection, kidney resection, skin defects, damage of veins and/or arteries, incisions made during surgery etc. The disclosure of applications, patents and publications, cited above or below, is hereby incorporated by reference.

The following examples are illustrative but not limiting.

EXAMPLES

Material and Methods

Thrombin. In the experiments below a thrombin component as in EVICEL® Fibrin Sealant (Manufactured by Omrix Biopharmaceuticals Ltd., Israel) was used.

Active Ingredient: Human thrombin (800-1200 IU/ml).

Other Ingredients: 40 mM Calcium chloride (CaCl$_2$), 6 mg/ml human albumin, 20 gr/L D-Mannitol, 20 mM Sodium acetate, 130 mM Sodium chloride (NaCl), Water for injection (WFI).

Pectin. In the experiments below Low Methoxyl (LM; two different kinds) and High Methoxyl (HM) pectin were used to prepare a pad comprising thrombin:

1. LM Pectin (Cat #104 AS, CPkelco, Atlanta, Ga.), degree of Esterification 27%, degree of Amidation 20% (referred to herein as "Kind 1"). Extracted from citrus peel.
2. LM Pectin (Cat #104 AS FS CPkelco, Atlanta, Ga.), degree of Esterification 26%, degree of Amidation 22% (referred to herein as "Kind 2"). Extracted from citrus peel.
3. HM pectin (Cat #76282, Sigma Aldrich, Rehovot, Israel) degree of Esterification 70-75%. Extracted from apple.

All pectin types were provided by the supplier as powders.

Table 1 lists HM and LM pectin properties.

TABLE 1

| Pectin properties. | | |
|---|---|---|
| | Degree of Esterification* [%] | Degree of Amidation** [%] |
| HM pectins | 60-75 | Not relevant |
| LM pectins | 20-40 | 10-30 |

*Degree of Esterification - the ratio between the esterified GalA monomers and the total GalA monomers.
**Degree of Amidation - the ratio between the amidated GalA monomers and the total GalA monomers.

Lyophilization. Lyophilization of the gel substance was carried out according to the cycle shown in Table 2 below using Christ Epsilon 2-8D lyophilizer. Following the lyophilization, a "solid cake" was obtained. The terms "cake", "solid cake" and "dry composition" refer to a porous and spongy structure-like composition resulting from the lyophilization process.

Typically, following the lyophilization process the cake supports its own structure i.e. the structure and volume of the gel substance and of the solid substance obtained after the lyophilization are substantially the same.

TABLE 2

| Lyophilization cycle. | | | | | |
|---|---|---|---|---|---|
| Section | Phase | Time (h:m) | Temp. (° C.) | Vacuum (mBar) | Chamber Pressure (mBar) |
| 1 | Start values | —:— | 4 | OFF | OFF |
| 2 | Freezing | 01:00 | −30 | OFF | OFF |
| 3 | Freezing | 01:00 | −50 | OFF | OFF |
| 4 | Freezing | 05:40 | −50 | OFF | OFF |
| 5 | Preparation | 00:20 | −45 | OFF | OFF |
| 6 | Sublimation | 00:15 | −40 | 0.2 | 800 |
| 7 | Sublimation | 00:15 | −25 | 0.2 | 800 |
| 8 | Sublimation | 25:00 | −25 | 0.2 | 800 |
| 9 | Sublimation | 01:00 | −15 | 0.2 | 800 |
| 10 | Sublimation | 12:00 | −15 | 0.2 | 800 |
| 11 | Sublimation | 02:00 | 20 | 0.2 | 800 |
| 12 | Sublimation | 05:00 | 20 | 0.2 | 800 |

TABLE 2-continued

Lyophilization cycle.

| Section | Phase | Time (h:m) | Temp. (° C.) | Vacuum (mBar) | Chamber Pressure (mBar) |
|---|---|---|---|---|---|
| 13 | Second drying | 00:30 | 25 | 0.012 | 800 |
| 14 | Second drying | 18:00 | 25 | 0.012 | 800 |

Quantification of water content within the dry pad. Water content determination was carried out using the volumetric Karl Fischer Titration Method (KFT), which is based on the US Pharmacopoeia assay (USP 27, <921>, P. 2398-2399). Prior to the titration, the water was extracted from the lyophilized composition by adding 4 ml dried methanol into a vial holding the lyophilized composition and rolling the vial for 30 minutes at room temperature. Then, 3 ml from the supernatant were taken for the titration.

Assessing the hemostatic efficacy of the pads using in-vivo models.

Rat kidney hemorrhage model—a model of severe or brisk bleeding:

The efficacy was determined using the in-vivo acute rat kidney hemorrhage model.

Sprague dawley rats at ages of about 3 months and weighing about 350 gr were used in this model. Anesthesia was induced with 50 mg pental/kg administered by IP (Intraperitoneal) injection. During the procedure the effect of the anesthesia was monitored and if necessary an additional injection of pental was administrated.

To maintain the animal at a constant temperature of between 38° C. and 40° C. (optimally 38.4° C.), the animal was placed on a thick plastic operating board and both a heating lamp and an electric heating pad coupled to a thermo probe were placed underneath the board (thermo regulator).

The animal was shaved on the left flank for a paralumbar laparotomy. The shaved site was wiped with 70% alcohol. A thermoprobe was inserted into the animal's rectum to monitor the temperature. The animal was turned to a right dorsolateral position. A bolus of Heparin (RotexMedica Germany #ET3L184-10-200 IU/kg) was injected intravenously in order to prevent activity of endogenous thrombin present in the blood of the animal (the heparin concentration administered did not affect thrombin present within the pad). By using this model, reproducibility is maintained as animals cannot activate their internal clotting mechanism via endogenous thrombin.

A left paralumbar incision in the size of about 1-2 cm was made from the left hip to the twelfth rib and the left kidney was exposed. The kidney was separated from the perirenal fat. The rat was repositioned in dorsal recumbency. The renal vessels were occluded with a soft vascular clamp. A sagital heminephrectomy was performed, removing the entire distal half of the kidney perpendicular to the renal vessels. The cut's surface of the remaining kidney was blotted dry. The tested pad was applied onto the cut surface of the kidney. Three minutes were allowed to lapse for polymerization before releasing the renal clamp. After releasing the renal clamp, the kidney was observed for incidence of bleeding. If bleeding occurred, the blood was allowed to be absorbed within the pads for a period of one hour.

If the animal lived for the entire hour test period, the pad was removed to assess bleeding from the kidney by subtracting the weight of the pad after application onto the cut from the weight of the pad prior to application. Immediately after the pad was removed the surviving animals (still under anesthesia) were euthanized using $CO_2$.

Swine spleen hemorrhage model—a model of mild to moderate bleeding.

The procedure was carried out essentially as described in Cole D J et al. "A pilot study evaluating the efficacy of a fully acetylated poly-N-acetyl glucosamine membrane formulation as a topical hemostatic agent". Surgery. 1999 September; 126(3):510-7 with the following exceptions:

1—the wound was inflicted by using a 4 mm biopsy punch needle and generating a circular defect within the spleen (and not by creating an incision in the spleen as in Cole D J et al.); and 2—the pad application procedure was carried out as follows: the wound was allowed to bleed freely for 5 seconds before removal of accumulated blood by gentle pressure with a surgical sponge. The hemostatic agent being tested (either pectin-thrombin pad or control treatment: SURGIFOAM® Absorbable Gelatin Sponge immersed in thrombin solution; see Example 4 below for exact formulations) was applied with direct digital pressure for 30 seconds followed by observation without pressure for 60 seconds. If the wound continued to bleed or re-bleed, the agent already applied was left in place without addition of further agent, and the above described cycle of pressure (30 seconds followed by observation for 60 seconds) was repeated for a second time. This cycle was repeated for a total of 5 minutes from the generation of the wound. If hemostasis was not achieved within 5 minutes the test was declared as fail. In this experiment, the time to hemostasis (up to 5 min) following application of the pad/sponge onto the bleeding site was measured and recorded for each trial. Pectin Percent Concentrations used throughout the application are Weight per Volume (w/v).

For liquid and gel substance, 1% w/v pectin means pectin at concentration of 10 g/L.

For dry pads, 1% w/v pectin means pectin at a density of 10 mg/cm$^3$.

Example 1

Preparation of a Dry Thrombin-Pectin Pad Using Different LM Pectin Concentrations Pads comprising about 1-10% (w/v) (10-100 mg/cm$^3$) LM pectin and thrombin were prepared generally as described below; preparation of a pad comprising 3% (w/v) (30 mg/cm$^3$) LM pectin is described below in more detail.

As a first step, different pectin stock solutions having a concentration of about 1.5 to 15% (w/v) (15-150 g/L) were prepared by dissolving LM pectin powder (Kind 1 as defined above; in the amount listed in Table 3 below) in 48.5 ml DDW at 40-70° C. while stirring at 1300 RPM for 3-6 hours until the solution was homogenous as determined by a visual inspection. A solution having a pH of 3.5-5.5 was obtained. Next, 0.5M NaOH was added to form a pH of about 7.0 (the specific titration volume is listed in Table 3 below).

The specific pectin powder weight and titration volume of NaOH used to prepare the different pectin stock solutions are specified in Table 3 below.

TABLE 3

Preparation of Pectin Stock Solutions.

| Pectin stock solution Concentration [%] (w/v) | LM Pectin powder (Kind 1) [gr] | 0.5M NaOH used for titration [ml] |
|---|---|---|
| 1.5 | 0.75 | 1.0 |
| 4.5 | 2.25 | 2.0 |
| 7.5 | 3.75 | 2.5 |
| 10.5 | 5.25 | 2.5 |
| 15 | 7.50 | 2.5 |

In the next step, the pectin stock solutions were stored at 4° C. overnight (14-18 hours) for stabilization of the pectin solution.

In the next step, 1.7 ml thrombin (from EVICEL® Fibrin Sealant as described above) and 25 µl 10.8M calcium chloride ($CaCl_2$) were mixed together and then the formed mixture was mixed with 3.3 ml of each pectin stock solution—1.5, 4.5, 7.5, 10.5 and 15%—to form pectin gels having a final pectin concentrations of about 1, 3, 5, 7 and 10% (w/v) (10-100 g/L), respectively. Mixing of the thrombin with $CaCl_2$ and then with pectin stock solution was carried out at room temperature (20-25° C.). Mixing of the thrombin-$CaCl_2$ solution with the pectin solution was carried out using two syringes (see elaboration below), the solutions were transferred between the two syringes 10-15 times. A final volume of 5 ml was obtained and the final mixture was poured into a lyophilization glass cup having the following dimensions: 25 mm height and 25 mm in diameter. The lyophilization glass cup was placed in the lyophilizer and lyophilized according to Table 2 above to form a dry pad having a water content of ≤3% as measured by Karl Fischer Titration Method. The different dry pads (after the lyophilization step) comprised a density of about: 1, 3, 5, 7 or 10% (w/v) (10-100 mg/cm³) pectin, 340 IU/cm³ thrombin and 7.5 mg/cm³ calcium. The height of the dry pads was in the range of 10-14 mm and 25 mm in diameter.

Elaboration of the preparation method of a dry pad comprising a density of 3% (w/v) pectin (30 mg/cm³):

2.25 gr LM pectin powder (Kind 1 as defined above) was dissolved in 48.5 ml DDW thereby obtaining a pectin stock solution at a concentration of 4.5% (w/v). The dissolution was carried out at 40° C.-70° C. with stirring at 1300 RPM for 3-6 hours (until the solution was homogenous as determined by a visual inspection). A solution having a pH of 3.5-5.5 was obtained. After dissolution, the pectin stock solution was titrated with 0.5M NaOH (about 2 ml) to a pH of about 7.0.

In the next step, the pectin stock solution was stored at 4° C. overnight (14-18 hours) for stabilization of the pectin solution.

In the next step, 1.7 ml thrombin, which includes 40 mM $CaCl_2$, were mixed with 25 UI 10.8M $CaCl_2$ (obtaining a final $CaCl_2$ concentration of 67.5 mM in the thrombin solution). The thrombin-calcium mixed solution (about 1.7 ml) was then mixed with 3.3 ml pectin stock solution (having a concentration of 4.5% w/v) to form a gel. Mixing of the thrombin with $CaCl_2$ and then with pectin stock solution was carried out at room temperature (20-25° C.).

Mixing was carried out by using two 5 ml syringes connected to one another via a 3-way-stopcock (Cat 1097 Ilif, Haryana, India)—one syringe with the thrombin-calcium solution, and the other with the pectin stock solution. The solutions were transferred between the two syringes 10-15 times. Following mixing, the mixed solutions (5 ml in volume) were poured into lyophilization cups (see dimensions above), accessible bubbles formed on the upper surface of the gel were discarded using a needle, and the cups were then transferred into a lyophilizer and lyophilized according to Table 2 above.

The final density of pectin, thrombin and calcium in the formed pad was 3% (w/v) (30 mg/cm³), 340 IU/cm³ and 7.5 mg/cm³, respectively.

A pad comprising 3% (w/v) (30 mg/cm³) LM pectin Kind 1 and 7.5 mg/cm³ calcium (without thrombin) was prepared and served as a control for the below experiments/measurements. The control pad was prepared in the same manner as a pad comprising 3% (w/v) LM pectin, 340 IU/cm³ thrombin and 7.5 mg/cm³ except that instead of 1.7 ml thrombin solution, only the thrombin buffer component (1.7 ml Water for Injection comprising 6 mg/ml Human Albumin, 20 mM Sodium Acetate, 20 gr/L D-mannitol, 130 mM NaCl and 40 mM $CaCl_2$) was used.

Following the lyophilization procedure, the pads were stored in a closed compartment with a desiccant at room temperature (20-25° C.) (Sorb-It #4243 Süd-Chemie, Munich, Germany) until they were evaluated for their hemostatic efficacy and visually inspected for specific parameters.

A visual inspection for the following parameters was carried out for the above prepared gels (after mixing the content of the two syringes and pouring the content into the lyophilization cups and prior to the lyophilization itself):

The ranking for all parameters was done on a scale of 1 to 5 (1 being low to 5 being high); all evaluations were qualitative and the ranking was determined relative to other gel preparations; the optimal value for each parameter is indicated in brackets.

Bubbliness (1)—When evaluating this parameter, both the amount and size of the bubbles within the formed gel were considered. The presence of a large number of bubbles or of large bubbles within the gel preparation is undesired since it may result in a dry pad having large air cavities which are non-homogeneously distributed within the gel, negatively affecting hemostasis and the firmness of the dry pad.

Liquid above the gel (1)—This parameter was evaluated by tilting the cup comprising the gel and visually estimating the liquid volume above the gel. The presence of liquid above the formed gel is undesired since it is indicative of low homogeneity of the gel and consequently low homogeneity of the pad following its lyophilization.

Stickiness (4-5)—This parameter was evaluated by touching the gel with a Nitril glove and qualitatively evaluating the gel adherence to the glove. A high value of stickiness is desired since it is indicative of a high adherence of the dry pad, to be obtained after drying, to surfaces.

Rigidity (3-4)—This parameter was evaluated by gently manually compressing the gel. A value of 3-4 is desired since it is indicative of enough rigidity of a dry pad, to be obtained after drying, to maintain its structure but not too rigid so it could be manipulated or adapted to conform to the shape of a body organ.

The results of the visual inspections of the different gels are shown in Table 4 below.

TABLE 4

Characterization of the prepared gels.

| LM Pectin concentration [%] (w/v) | Bubbliness (1)* | Liquid above the gel (1)* | Stickiness (4-5)* | Rigidity (3-4)* |
|---|---|---|---|---|
| 1 | 4 | 5 (about 2 ml) | 2 | 1 |
| 3 | 3 | 3 (about 1 ml) | 2 | 2 |
| 3% LM Pectin with no thrombin (Control Pad) | 3 | 3 | 1 | 2 |
| 5 | 3 | 2 (about 1 ml) | 3 | 3 |
| 7 | 2 | 1 No liquid | 4 | 4.5 |
| 10 | 2 | 1 No liquid | 4 | 5 |

*The optimal value for each parameter.

A visual inspection was also carried out for the dry pads (after lyophilization). Following the lyophilization, a "solid cake"/"cake" was obtained. A "solid cake" refers to a porous and spongy structure-like composition resulting from the lyophilization process. The following parameters were evaluated; the ranking for all parameters was done on a scale from 1 (being low) to 5 (being high); all evaluations were qualitative and the ranking was determined relative to other gel preparations; the optimal value for each parameter is indicated in brackets:

Fragility (1)—This parameter was evaluated by gently compressing each pad and evaluating the pad's fractions left on the glove. The pads should advantageously maintain their structure and stay intact during manipulation and handling.

Foaminess (3)—This parameter relates to the foam like structure of the pad and was evaluated by gently applying pressure to the pad and evaluating the cavities within the pad (based on the ability/resistance to compress the pad). A value of 3 indicates a pad having a porosity that can absorb liquid/blood without blood escaping through the cake (see description of "cake" above).

Stickiness (4-5)—Evaluated as described above for the gel preparations. Sticky pads better adhere to the target tissue.

Rigidity/Stiffness (3)—This parameter was evaluated by gently manually compressing the pad and assessing the resistance to pressure. A value of 3 indicates a balance between a pad that can easily conform to the shape of the body but can still maintain its structure and not break.

Also, the density of each dry pad was mathematically calculated by dividing the total solids in the dry pad composition to the pad's volume (the gel substance volume used to prepare the dry pad which is substantially the same as the pad's volume; about 5 ml).

The total solids in the thrombin component solution are about 40 mg per ml. The results of the visual inspections and the calculated density of the different dry pads are shown in Table 5 below.

TABLE 5

Characterization of dry pads prepared with LM pectin.

| LM Pectin density [%] (w/v) | Fragility (1)* | Foaminess (3)* | Stickiness (4-5)* | Rigidity (3)* | Density [mg/cm$^3$] ** |
|---|---|---|---|---|---|
| 1 | 5 | 4 | 3 | 4 | 23.5 |
| 3 | 3 | 3 | 3 | 3 | 43.3 |
| 3% LM Pectin With no thrombin (Control Pad) | 2.5 | 2 | 3 | 3 | 30 |
| 5 | 2 | 3 | 3 | 3 | 63.1 |
| 7 | 1 | 1 | 2 | 2 | 82.9 |
| 10 | 1 | 1 | 2 | 2 | 112.6 |

*The optimal value for each parameter.
** Mathematically calculated.

The results show that according to the physical characteristics of the gels (Table 4), gels having an LM pectin concentration of 7% (w/v) were superior as compared to the other gels.

Surprisingly, physical characteristics of the dry pads (Table 5) showed that pectin pads having an LM pectin density of 7 and 10% (w/v) were inferior as compared to pads having lower pectin densities. Gels/pads having pectin density of 3 and 5% (w/v) LM pectin had optimal characteristics.

In the above preparation method, a thrombin-pectin gel was formed according to the following order in the procedure: thrombin was first mixed with the $CaCl_2$ and then combined and mixed with the pectin solution.

When the mixing order was changed and the $CaCl_2$ was first mixed with the pectin solution (and then with the thrombin solution), an immediate gelation occurred. This onset early gelation, generated gel drops and therefore lack of homogeneity within the pectin gel, which caused an inadequate mixing with the thrombin solution on the next step.

The results show that, in order to form a homogenous pad, it is advantageous to first mix the calcium with the thrombin solution, and in a next step to add the pectin solution.

Pads were also prepared from LM pectin Kind 2 (as defined above) in a similar manner as LM pectin Kind 1. A visual inspection for the gels and pads was carried out for the parameters specified above. The obtained results and the conclusions were similar to those of LM pectin Kind 1.

Example 2

Preparation of a Dry Thrombin-Pectin Pad Using Different HM Pectin Concentrations Pads comprising 0.66-5.33% (w/v) (6.6-53.3 mg/cm$^3$) HM pectin and thrombin were prepared as follows:

As a first step, a pectin stock solution having a concentration of 8% (w/v) (80 g/L) HM pectin was prepared as follows—100 ml 50 mM Sodium Bi Carbonate buffer (Cat #31437, Sigma Aldrich, Rehovot, Israel) were added into a mixer bowl and 8 gr HM pectin (as described in the Materials and Methods section above) were added gradually during mixing by using a mixer (Cat: K5SSWH 325 watt KitchenAid, St. Joseph, Mich.) at a speed of 280 RPM for about 30 minutes at room temperature (20-25° C.) until the pectin was completely dissolved—visually inspected—and a homogenous paste like solution with no clumps was formed. The paste like solution had a pH of about 3.0.

In the next step, the paste like solution was used to form different pectin concentrations—1, 2, 4, 6, and 7% (w/v) (10-70 g/L)—by diluting the 8% HM pectin stock solution with 50 mM Sodium Bi Carbonate in the volumes shown in Table 6 below (the total volume was 30 ml).

TABLE 6

Formation of a solution having different HM pectin concentrations.

| HM Pectin concentration (w/v) | 8% HM pectin Stock solution (ml) | Sodium Bi Carbonate 50 mM (ml) | Total volume (ml) |
|---|---|---|---|
| 1% pectin | 3.75 | 26.25 | 30 |
| 2% pectin | 7.5 | 22.5 | 30 |
| 4% pectin | 15 | 15 | 30 |
| 6% pectin | 22 | 8 | 30 |
| 7% pectin | 25 | 5 | 30 |
| 8% pectin | 30 | 0 | 30 |

In the next step, a thrombin solution (as described in the Materials and Methods section) was added to the different pectin solutions (including the 8% pectin stock solution) at a ratio of 1:2 [15 ml thrombin solution and 30 ml pectin solution]. Since HM pectin requires saccharides for gelation (the Mannitol concentration in the thrombin component was not sufficient to form a gel substance), the solution formed was in a liquid state, and not in a gel form. It was observed that the formed solution was viscous and only partially homogeneous.

5 ml of the obtained mixture was poured into a lyophilization glass cup (having a height of 25 mm and a diameter of 25 mm) and lyophilized according to the lyophilization cycle described in Table 2. The final pectin density in the different dry pads was: 0.66%, 1.33%, 2.66%, 4%, 4.66%, 5.33% (w/v) (6.6-53.3 $mg/cm^3$); the thrombin density was 333 $IU/cm^3$; and the calcium density was 1.48 $mg/cm^3$. The height of the dry pads was in the range of 9-10 mm and 25 mm in diameter.

Following the lyophilization procedure, the pads were stored in a closed compartment with a desiccant at room temperature (20-25° C.) (Sorb-It #4243 Süd-Chemie, Munich, Germany) until they were evaluated for their hemostatic efficacy and for the following characteristics: fragility, foaminess, stickiness and rigidity using the above ranking as in Example 1. In these pads a visual inspection was carried out only for the dry pads.

Also, the density of each dry pad was mathematically calculated as described for the LM pectin pads (the gel substance volume was 5 ml).

The density and the value of each inspected parameter are shown in Table 7 below.

TABLE 7

Characteristics of dry pads prepared with HM pectin.

| HM pectin density [%] (w/v) | Fragility (1)* | Foaminess (3)* | Stickiness (4-5)* | Rigidity (3)* | Density [mg/cm³]** |
|---|---|---|---|---|---|
| 0.66 | 1-2 | 1-2 | 1 | 5 | 22.8 |
| 1.33 | 1-2 | 1-2 | 1 | 5 | 29.4 |
| 2.66 | 1-2 | 1-2 | 1 | 5 | 42.8 |
| 4 | 1-2 | 1-2 | 1 | 5 | 55.2 |
| 4.66 | 1-2 | 1-2 | 1 | 5 | 60.5 |
| 5.33 | 1-2 | 1-2 | 1 | 5 | 69.4 |

*The optimal value for each parameter.
**Mathematically calculated.

The results show that the HM pectin density within the pad had no effect on the above tested characteristics (all pads received the same ranking).

It was also shown that these pads were non-homogeneous and comprised solid crystals (as visually observed).

These results suggest that pads comprising HM pectin and prepared under the above conditions will have a poor absorbance quality, will not be easily manipulated and conformed to the shape of the body organ, will not adhere efficiently to the target tissue, and thus will not be efficient in stopping bleeding.

Example 3

In-Vivo Hemostatic Efficacy of HM and LM Pectin-Thrombin Pads in Acute Rat Kidney Hemorrhage Model The following example was aimed to determine the hemostatic efficacy of thrombin-pectin pads prepared according to Examples 1 and 2 in a severe bleeding model. The evaluation was carried out using the in-vivo acute rat kidney hemorrhage model described above.

Dry pads comprising the following LM pectin densities were tested—1%, 3%, 5%, 7% and 10% (w/v), and pads comprising the following HM pectin densities were tested: 0.66%, 1.33%, 2.66% and 4.66% (w/v).

The calcium and thrombin densities in the LM pectin pads were: 7.5 $mg/cm^3$ and 340 $IU/cm^3$, respectively.

The calcium and thrombin densities in the HM pectin pads were: 1.48 $mg/cm^3$ and 333 $IU/cm^3$, respectively.

In this experiment, the performance of a pad comprising 3% (w/v) LM pectin and 7.5 $mg/cm^3$ calcium (without thrombin) prepared as elaborated in Example 1 was also tested.

Hemostaticly efficient pads were considered as pads which achieved a blood loss of about 4 gr or less.

The blood loss results and the average value when using the different pectin pads are presented in Table 8 (for pads comprising LM pectin) and Table 9 (for pads comprising HM pectin) below.

TABLE 8

Average blood loss in a rat kidney model when using pads comprising different LM pectin densities.

| Tested Pad Pectin densities (%) (w/v) | Average Blood Loss [gr]*** |
|---|---|
| 3% Pectin* (control pad with no thrombin) | 8.82 (8.321, 8.904, 9.262) |
| 1% Pectin* | 3.25 (4.368, 4.088, 1.296) |
| 3% Pectin* | 3.17 (2.832, 4.243, 2.420) |
| 3% Pectin** | 3.53 (3.030, 4.017) |
| 5% Pectin* | 7.53 (5.77, 8.614, 8.215) |
| 7% Pectin* | 5.80 (6.366, 4.645, 6.371) |
| 10% Pectin* | 6.36 (4.923, 7.243, 6.921) |

*Kind 1 LM Pectin was used (as defined above).
**Kind 2 LM Pectin was used (as defined above).
***In brackets appearing are the individual blood loss results for each treatment.
**** Number of animals tested = 2-3.

TABLE 9

Average blood loss in a rat kidney model when using pads comprising different HM pectin densities.

| Tested Pad Pectin densities (%) (w/v) | Average Blood Loss [gr]** |
|---|---|
| Pectin 0.66% | 7.11 |
| Pectin 1.33% | 7.41 |
| Pectin 2.66% | 7.53 (7.099, 7.979) |
| Pectin 4.66% | 9.57 |

* Number of animals tested = 1-2.
**In brackets appearing are the individual blood loss results for each treatment.

The results show that pads comprising 1% and 3% (w/v) LM pectin (both Kind 1 and 2) had an acceptable average blood loss of lower than 4 gr (see Table 8). The results also show that pads comprising 3% (w/v) LM pectin with no thrombin had a non-acceptable high blood loss (see Table 8).

None of the HM pectin pads achieved an acceptable haemostatic effect, all showing unacceptable high blood loss (see Table 9).

These results show that a pectin pad should advantageously comprise thrombin and equal to or higher than 1% to lower than 5% (w/v) LM pectin in order to obtain a pad which is capable of effectively stop severe bleeding.

Example 4

In-Vivo Hemostatic Efficacy of LM Pectin-Thrombin Pads in a Swine Spleen Hemorrhage Model The previous example showed that a pad comprising thrombin, and LM pectin at densities of 1 and 3% (w/v) effectively stopped severe bleeding. The following example was aimed to assess the efficacy of different thrombin-LM pectin pads in stopping mild to moderate bleeding.

In this example a swine spleen hemorrhage model was used as described above. As indicated above, the time to hemostasis (up to 5 min) was recorded for each trial. The acceptable criterion for success is a time to hemostasis of 300 seconds or less.

The tested pads comprised pectin at densities in the range from 1-5% (w/v); thrombin densities of 340 and 680 IU/cm$^3$; and calcium densities of 4.5 and 7.5 mg/cm$^3$.

The pads were prepared as follows:

A 10% (w/v) pectin solution was prepared by dissolving 5 gr LM pectin powder (Kind 1 as defined above) in 40 ml DDW. The pectin powder was added gradually into the DDW, the dissolution step was carried out at a temperature of 40° C.-70° C. while stirring at 1300 RPM for 3-6 hours. Following dissolution, the pH of the obtained solution was 5.0, and titration was carried out with about 2 ml 0.5M NaOH to obtain a pH of about 7.0. In the next step, DDW was added to the solution to a final volume of 50 ml. The pectin stock solution was stored at 4° C. overnight (14-18 hours) for stabilization.

Then, thrombin solution, that contains 40 mM CaCl$_2$, was mixed with 25 µl of 2.7M CaCl$_2$ (yielding a final calcium concentration of 27 mM within the thrombin solution). The thrombin-calcium solution was then mixed with DDW (see thrombin solution and DDW volume for each pad in Table 10 below).

The above solution was then mixed with the pectin stock solution to form a pectin-thrombin gel (see 10% w/v pectin stock solution volume for each pad in Table 10 below). Mixing was carried out at room temperature as described in Example 1.

TABLE 10

Volumes used for the preparation of LM pectin-thrombin gels.

| Final Pectin density w/v within the dry pad | Pectin* Stock solution 10% w/v [ml] | Thrombin-calcium solution [ml] | DDW [ml] |
|---|---|---|---|
| 1% | 0.5 | 1.7 | 2.8 |
| 3% | 1.7 | 1.7 | 1.7 |
| 3% | 1.7 | 3.4 | — |
| 5% | 2.5 | 1.7 | 0.8 |

*Kind 1 LM pectin was used.

Following mixing within the two syringes, the solutions (about 5 ml) were transferred into lyophilization cups (see dimensions above), placed into a lyophilzer and lyophilized according to the cycle elaborated in Table 2.

The final pectin, thrombin and calcium densities are listed in Table 11. The dry pads had the following dimensions: a height—in the range of 8-12 mm and a diameter of 25 mm.

TABLE 11

Pectin, thrombin and calcium densities within the dry pad.

| Pad # | Pectin density within the dry pad (w/v) | Thrombin (IU/cm$^3$) | Calcium (mg/cm$^3$) |
|---|---|---|---|
| 1 | 1 | 340 | 7.5 |
| 2 | 3 | 340 | 7.5 |
| 3 | 3 | 680 | 4.5 |
| 4 | 5 | 340 | 7.5 |

As a positive control, SURGIFOAM® Absorbable Gelatin Sponge was used with thrombin (prepared as indicated below). SURGIFOAM® sponge is a sterile, water-insoluble, malleable, porcine gelatin absorbable sponge intended for hemostatic use by applying to a bleeding surface. The sponge is off-white and porous in appearance. In this experiment, prior to use SURGIFOAM® (having a height of 10 mm) was cut into a size of 20×30 mm, saturated in 2 ml thrombin solution (a thrombin component as in EVICEL® fibrin sealant diluted as follows: 1 ml thrombin component: 4 ml Saline). Prior to its application the saturated sponge was squeezed between gloved fingers to expel air bubbles, and applied according to the procedure elaborated in the model above.

The average times to hemostasis achieved when using the different pectin pads and the control treatment (SURGIFOAM® with thrombin) are presented in Table 12 below. As indicated above, an acceptable time to hemostasis is 300 seconds or less.

TABLE 12

Average time to hemostasis in a swine spleen hemorrhage model when using pads comprising different LM pectin, calcium and thrombin densities.

| Pad # | Pectin density within the dry pad (w/v) | Thrombin (IU/cm$^3$) | Average Time to hemostasis (seconds)* |
|---|---|---|---|
| 1 | 1 | 340 | 240 (180, 300) |
| 2 | 3 | 340 | 300 |

TABLE 12-continued

Average time to hemostasis in a swine spleen hemorrhage model when using pads comprising different LM pectin, calcium and thrombin densities.

| Pad # | Pectin density within the dry pad (w/v) | Thrombin (IU/cm$^3$) | Average Time to hemostasis (seconds)* |
|---|---|---|---|
| 3 | 3 | 680 | 30 |
| 4 | 5 | 340 | 75 (120, 30) |
| Positive Control treatment | — | | 30 (30, 30, 30) |

*In brackets appearing are the individual Time to hemostasis results for each treatment.
** Number of animals tested = 1-3.

The results show that all tested pads effectively stopped bleeding in this model i.e. had a time to hemostasis of 300 seconds or less.

The results also show that pads comprising 3% (w/v) pectin with 680 IU/cm$^3$ thrombin achieved optimal results with a time to hemostasis of 30 seconds-similar to the result of a the control treatment (SURGIFOAM® with thrombin) which is currently the standard operating procedure in clinical settings.

These results show that performance of a pectin pad may be enhanced by increasing the thrombin density e.g. see the performance of a pad comprising 3% (w/v) pectin and 340 IU/cm$^3$ thrombin vs. the performance of a pad comprising 3% (w/v) pectin and 680 IU/cm$^3$ thrombin.

The invention claimed is:

1. A conformable hemostatic dry pad having a spongy-like structure, produced through lyophilization, comprising:
   i) pectin,
   ii) calcium cation, and
   iii) thrombin, and
   1) wherein the pectin is low methoxy] (LM) pectin and has a density in the dry pad higher than 1% to lower than 5% (w/v),
   2) wherein the hemostatic dry pad is free of an animal derived substance selected from the group consisting of collagen and gelatin,
   3) wherein the thrombin and pectin are mixed and uniformly dispersed throughout the dry pad, and
   4) wherein the thrombin in the pad is non-covalently bound thrombin.

2. The pad according to claim 1, wherein the pectin density is from about 3% to lower than 5% (w/v).

3. The pad according to claim 1, wherein the pectin density is about 3% (w/v).

* * * * *